(12) United States Patent
Hammer et al.

(10) Patent No.: US 9,283,004 B2
(45) Date of Patent: Mar. 15, 2016

(54) ROD ATTACHMENT ASSEMBLY FOR OCCIPITAL PLATE

(71) Applicant: BLACKSTONE MEDICAL, INC., Lewisville, TX (US)

(72) Inventors: Michael Hammer, Pine Brook, NJ (US); Tara Ziolo, Hewitt, NJ (US); Stephen Termyna, Boonton, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 0 days.

(21) Appl. No.: 14/532,688

(22) Filed: Nov. 4, 2014

(65) Prior Publication Data

US 2015/0052729 A1 Feb. 26, 2015

Related U.S. Application Data

(62) Division of application No. 13/767,403, filed on Feb. 14, 2013.

(51) Int. Cl.
*A61B 17/70* (2006.01)
*B23P 11/00* (2006.01)

(52) U.S. Cl.
CPC .......... *A61B 17/7059* (2013.01); *A61B 17/7044* (2013.01); *A61B 17/7055* (2013.01); *Y10T 29/49826* (2015.01)

(58) Field of Classification Search
CPC ........... A61B 17/7055; A61B 17/7059; A61B 17/7032; A61B 17/7037; A61B 17/7044
USPC ................. 606/60–78, 279; 29/428
See application file for complete search history.

(56) References Cited

U.S. PATENT DOCUMENTS

| | | | |
|---|---|---|---|
| 6,540,748 B2 | 4/2003 | Lombardo | |
| 6,547,790 B2 | 4/2003 | Harkey, III et al. | |
| 7,232,441 B2 | 6/2007 | Altarac et al. | |
| 7,618,443 B2* | 11/2009 | Abdou | 606/278 |
| 7,621,942 B2 | 11/2009 | Piehl | |
| 7,695,500 B2 | 4/2010 | Markworth | |
| 7,776,070 B2 | 8/2010 | Null et al. | |
| 7,901,433 B2* | 3/2011 | Forton et al. | 606/250 |
| 8,062,339 B2 | 11/2011 | Hammer et al. | |
| 8,226,695 B2* | 7/2012 | Moore et al. | 606/286 |
| 8,394,131 B2* | 3/2013 | Wing et al. | 606/280 |
| 8,894,695 B2* | 11/2014 | Moore et al. | 606/286 |
| 2003/0135213 A1* | 7/2003 | LeHuec et al. | 606/69 |
| 2003/0153913 A1* | 8/2003 | Altarac et al. | 606/61 |
| 2007/0118121 A1 | 5/2007 | Purcell et al. | |
| 2008/0086124 A1* | 4/2008 | Forton et al. | 606/60 |
| 2008/0125781 A1* | 5/2008 | Hoffman et al. | 606/69 |

(Continued)

OTHER PUBLICATIONS

International Search Report and Written Opinion, PCT/US2014/016378, dated May 13, 2014, 8 pages.

*Primary Examiner* — Jacqueline Johanas
(74) *Attorney, Agent, or Firm* — Baker & McKenzie LLP

(57) ABSTRACT

The present disclosure relates, according to some embodiments, to orthopedic implantable device technology, and more specifically to implantable devices for use in stabilizing the occipitocervical junction and the cervical spine. For example, the disclosure relates to embodiments of an implantable orthopedic assembly generally comprising an occipital plate and one or more repositionable clamping assemblies for securing a stabilizing rod at a nonzero distance from a plate surface. One or more rails may extend laterally from a plate to support a clamping assemblies.

18 Claims, 6 Drawing Sheets

(56) References Cited

U.S. PATENT DOCUMENTS

| | | |
|---|---|---|
| 2008/0147123 A1 | 6/2008 | Schermerhorn |
| 2008/0177314 A1 | 7/2008 | Lemoine |
| 2009/0270924 A1 | 10/2009 | Wing et al. |
| 2009/0312801 A1 | 12/2009 | Lemoine et al. |
| 2010/0010541 A1 | 1/2010 | Boomer et al. |
| 2010/0030279 A1* | 2/2010 | Flynn et al. ............. 606/305 |
| 2010/0036417 A1* | 2/2010 | James et al. ............. 606/246 |
| 2010/0125302 A1* | 5/2010 | Hammill et al. ......... 606/308 |
| 2010/0137920 A1* | 6/2010 | Hammill et al. ......... 606/308 |
| 2010/0222779 A1 | 9/2010 | Ziemek et al. |
| 2010/0228294 A1* | 9/2010 | LeHuec et al. ........... 606/264 |
| 2010/0256681 A1 | 10/2010 | Hammer et al. |
| 2010/0324557 A1 | 12/2010 | Cheema et al. |
| 2011/0190824 A1* | 8/2011 | Gephart et al. .......... 606/278 |
| 2012/0016425 A1* | 1/2012 | Shaffrey et al. .......... 606/305 |
| 2012/0065686 A1 | 3/2012 | Black et al. |
| 2012/0209335 A1* | 8/2012 | Termyna et al. ......... 606/300 |
| 2013/0131734 A1* | 5/2013 | Longtain et al. ......... 606/305 |
| 2013/0172936 A1* | 7/2013 | Berrevoets et al. ....... 606/278 |
| 2013/0172938 A1 | 7/2013 | Ziolo et al. |
| 2014/0046375 A1 | 2/2014 | Ziolo et al. |
| 2014/0277152 A1* | 9/2014 | Hammer et al. .......... 606/265 |

* cited by examiner

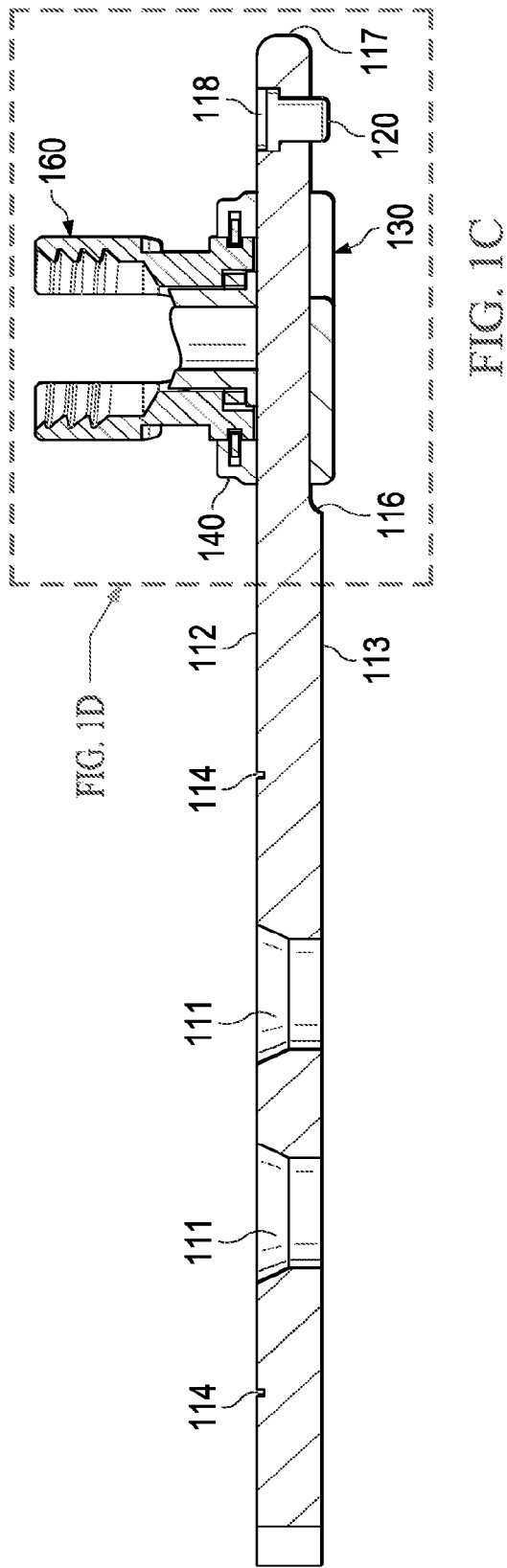

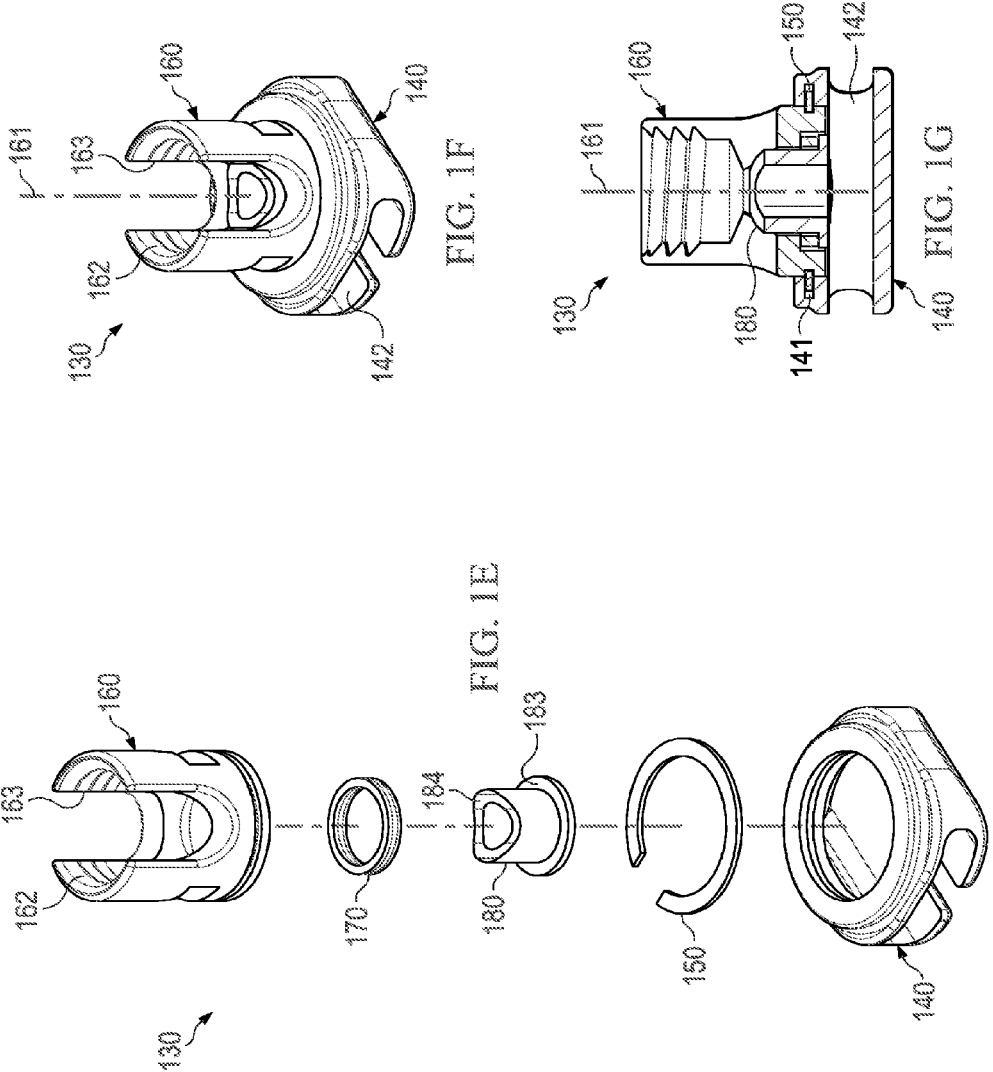

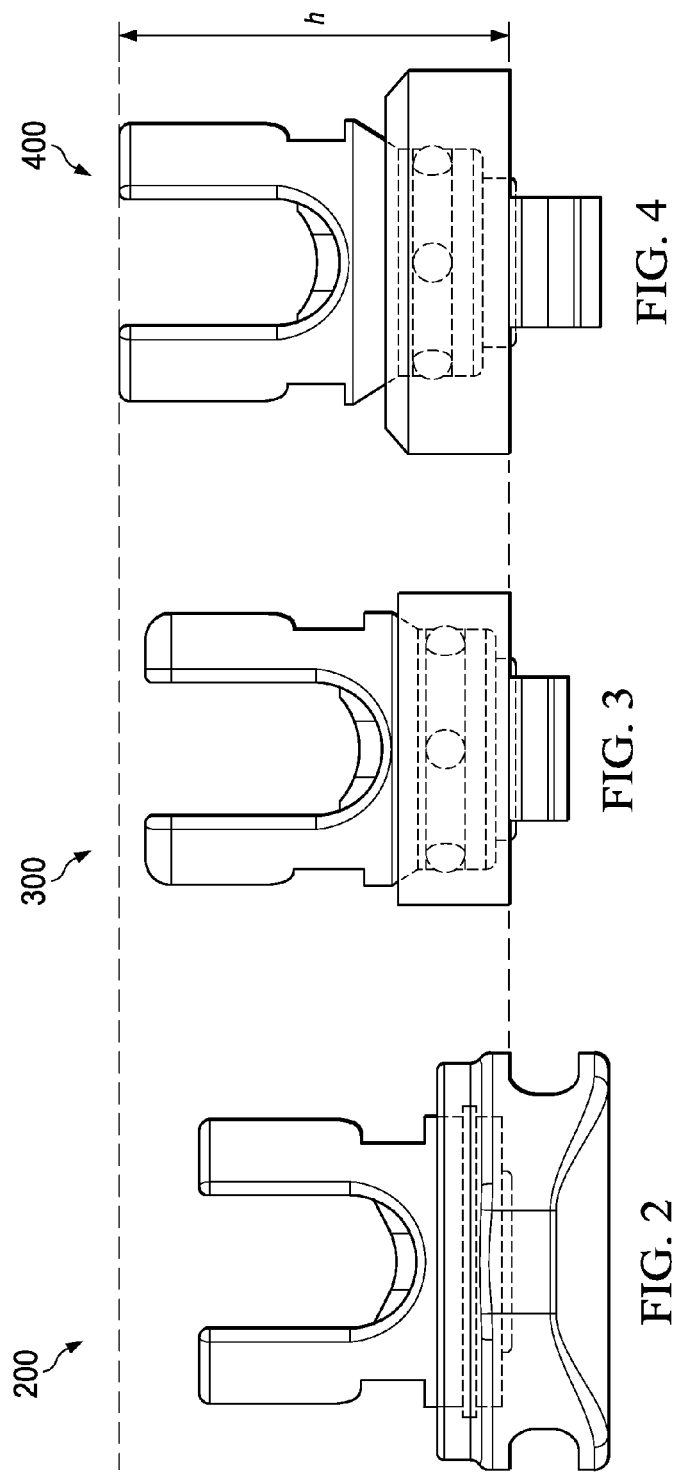

ROD ATTACHMENT ASSEMBLY FOR OCCIPITAL PLATE

CROSS REFERENCE TO RELATED APPLICATION(S)

This is a divisional application of U.S. application Ser. No. 13/767,403, which was filed on Feb. 14, 2013 and is incorporated herein by reference.

FIELD OF THE DISCLOSURE

The present disclosure relates, in some embodiments, to orthopedic implantable device technology, and more specifically to implantable devices for use in stabilizing the occipitocervical junction and the cervical spine.

BACKGROUND OF THE DISCLOSURE

In the human body, the lower back portion of the skull is known as the occiput, and the neck vertebrae located closest to the skull are known as the cervical spine. Critical neurological and vascular structures descending from the brain into the spinal column pass through the junction between the skull and the cervical spine (the occipitocervical junction). When disease or traumatic injury threatens the stability of the cervical spine and/or the occipitocervical junction, surgical intervention may be required to protect these critical structures.

Implantable occipitocervical fixation systems that provide stabilization and/or promote fusion of the occipitocervical junction are known in the art. However, existing systems may be difficult and time-consuming to adjust, and often fail to provide desirable configurability options.

SUMMARY

Accordingly, a need has arisen for improved an implantable occipitocervical fixation system that simplifies and streamlines surgical placement procedures and provides greater configurability to accommodate varying patient anatomies during surgical placement.

The present disclosure relates, in some embodiments, to orthopedic implantable device technology, and more specifically to implantable devices for use in stabilizing the occipitocervical junction and the cervical spine. For example, the disclosure relates to embodiments of an implantable orthopedic assembly generally comprising an occipital plate and one or more repositionable clamping assemblies (e.g., rod attachment assemblies) for securing a stabilizing rod at a nonzero distance from a plate surface. One or more rails may extend laterally from a plate to support a clamping assembly. In some embodiments, an implantable orthopedic assembly may comprise (a) an occipital plate comprising a top surface and a bottom surface, the bottom surface of the occipital plate adapted for securing to an occiput, (b) at least one rail extending laterally from a proximal portion of the occipital plate, the at least one rail comprising a top surface and a bottom surface, and/or (c) at least one repositionable rod attachment assembly adapted to enclose a portion of the at least one rail, the rod attachment assembly further adapted for securing a portion of a stabilizing rod at a distance from the at least one rail. A rod attachment assembly may comprise, in some embodiments, (1) a slide body comprising a rail aperture adapted to frictionally contact at least one surface of the at least one rail, the slide body further adapted for lateral repositioning between a first rail position and a second rail position, (2) a saddle body adapted for repositioning between a first rotational position and a second rotational position, the saddle body further adapted to receive the portion of the stabilizing rod, (3) a retention ring positioned on (e.g., contacting) an outside circumference of the saddle body (e.g., an outside circumference of a circumferential recess in the saddle body) and positioned on (e.g., contacting) an inside circumference of the slide body (e.g., an inside circumference of a circumferential recess in the slide body), the retention ring adapted to secure the saddle body to the slide body, (4) a pressure cap adapted to maintain alignment between a stabilizing rod and a saddle body (e.g., a corresponding stabilizing rod slot on the saddle body) and transfer an immobilizing force from the received portion of the stabilizing rod to the top surface of the at least one rail, the immobilizing force immobilizing the rod attachment assembly at a fixed rail position and in a fixed rotational position.

According to some embodiments, an occipital plate may comprise (e.g., further comprise) at least one groove scoring at least one of the top surface of the occipital plate or the bottom surface of the occipital plate, the at least one groove adapted to facilitate contouring of the occipital plate. Grooves may or may not be aligned (e.g., parallel) to each other. For example, an occipital plate may comprise a first groove and a second groove, with the second groove substantially orthogonal to the first groove.

An implantable orthopedic assembly, according to some embodiments, may comprise a plurality of apertures variably distributed across an occipital plate, wherein the plurality of apertures penetrates both the top surface of the occipital plate and the bottom surface of the occipital plate, and wherein at least one of the plurality of apertures is adapted to receive at least one bone fastener (e.g., bone screw), the at least one bone fastener adapted to secure the bottom surface of the occipital plate to the occiput. Apertures may independently have any desired shape. For example, a plurality of apertures may comprise a substantially circular first aperture centered about a first aperture center axis. Each aperture axis may be independently non-orthogonal to at least one of the top surface of the occipital plate and the bottom surface of the occipital plate. In some embodiments, a plurality of apertures may comprise at least one countersunk aperture.

An implantable orthopedic assembly may comprise at least one instrument interface adapted to facilitate manipulation of the occipital plate with an instrument, according to some embodiments. For example, an occipital plate may comprise an edge surface connecting a top surface of the occipital plate and a bottom surface of the occipital plate, wherein the at least one instrument interface comprises a notch in the edge surface of the occipital plate.

In some embodiments, an implantable orthopedic assembly may comprise an occipital plate having a longitudinal axis parallel to the plane of the occipital plate and defining a first side of the occipital plate and a second side of the occipital plate. An occipital plate may comprise, in some embodiments, at least one rail comprising a first rail and a second rail, for example, the first rail extending from the first side of the occipital plate, the second rail extending from the second side of the occipital plate.

A slide body of a repositionable rod attachment assembly, according to some embodiments, may be adapted for infinite lateral repositioning between a first rail position and a second rail position. A saddle body of a repositionable rod attachment assembly may be adapted for infinite rotational repositioning between a first body position and a second body position, according to some embodiments. A repositionable rod attachment assembly may comprise (e.g., further comprise) a loading component adapted to exert a stabilizing force on a pressure cap, the stabilizing force stabilizing the repositionable rod attachment assembly at an adjustable rail position and in an adjustable body position. A slide body may comprise a slot that is adapted to at least partially enclose a portion of a rail (e.g., the at least one rail). A rod attachment assembly may comprise (e.g., further comprise) a loading component (e.g., wave spring) adapted to be positioned between (e.g., in mechanical communication with) a saddle body and a pressure cap. A pressure cap may comprise, in some embodiments, a groove at one end adapted to contact at least a portion of a received portion of a stabilizing rod. According to some embodiments, an implantable orthopedic assembly may comprise a retaining element that is adapted to be attached to a plate rail and block egress from the plate rail (e.g., prevent a slide body from sliding off an end of the rail).

According to some embodiments, the present disclosure relates to methods of constructing an implantable orthopedic assembly. For example, a method may include constructing an implantable orthopedic assembly comprising an occipital plate, at least one rail rigidly coupled to and extending laterally from the occipital plate, and/or at least one repositionable rod attachment assembly enclosing a portion of the at least one rail, the at least one repositionable rod attachment assembly adapted for securing a received portion of a stabilizing rod. A method may comprise, in some embodiments, (a) positioning a pressure cap of a repositionable rod attachment assembly within a receptacle of a saddle body of the at least one repositionable rod attachment assembly, (b) positioning a surface of the at least one rail against a surface of a slide body of the at least one repositionable rod attachment assembly, (c) installing a retention ring in the slide body, (d) uniting the saddle body with the slide body, wherein the at least one rail contacts the pressure cap, and/or (e) securing the slide body to the saddle body with the retention ring. According to some embodiments, a method may comprise positioning a loading component between the pressure cap and the saddle body of the at least one repositionable rod attachment assembly, wherein the loading component is adapted to exert a bias on the pressure cap against the at least one rail to stabilize the at least one repositionable rod attachment assembly at an adjustable rail position and in an adjustable body position.

BRIEF DESCRIPTION OF THE DRAWINGS

Some embodiments of the disclosure may be understood by referring, in part, to the present disclosure and the accompanying drawings, wherein:

FIG. 1C illustrates a section view of an occipital-cervical fixation assembly according to a specific example embodiment of the disclosure;

FIG. 1E illustrates an exploded view of a rod attachment assembly according to a specific example embodiment of the disclosure;

FIG. 1F illustrates a perspective view of a rod attachment assembly according to a specific example embodiment of the disclosure;

FIG. 1G illustrates a section view of a rod attachment assembly according to a specific example embodiment of the disclosure;

FIG. 2 illustrates an elevation view of a rod attachment assembly according to a specific example embodiment of the disclosure;

FIG. 3 illustrates an elevation view of a rod attachment assembly according to a specific example embodiment of the disclosure; and FIG. 4 illustrates an elevation view of a rod attachment assembly according to a specific example embodiment of the disclosure.

Figure 1A:
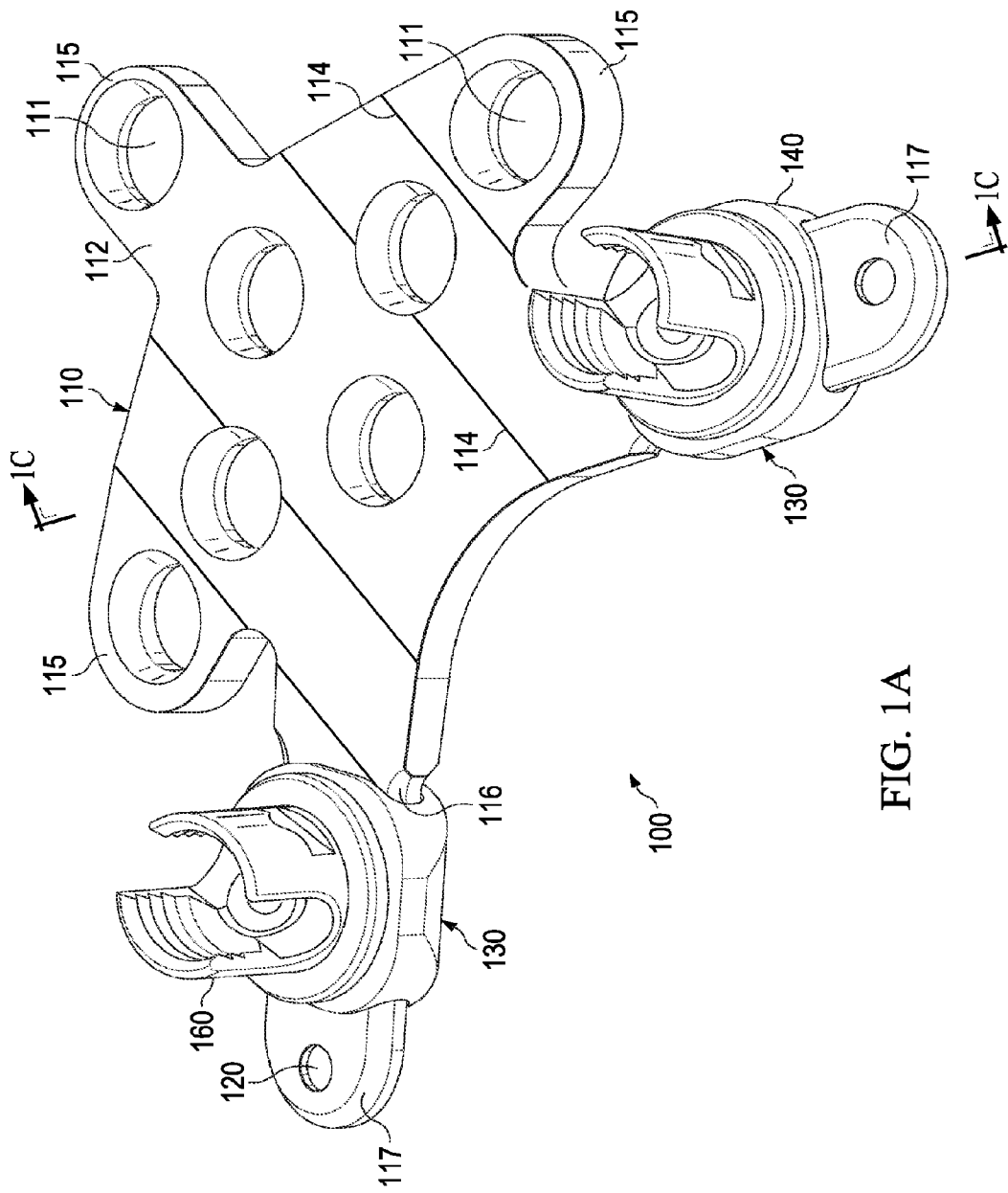
FIG. 1A illustrates a perspective view of an occipital-cervical fixation assembly according to a specific example embodiment of the disclosure.

Table 1 below includes the reference numerals used in this application. The thousands and hundreds digits correspond to the figure in which the item appears while the tens and ones digits correspond to the particular item indicated. Similar structures share matching tens and ones digits.

|  | FIG. 1 |
|---|---|
| Occipital Plate System | 100 |
| Plate | 110 |
| Aperture | 111 |
| Upper Surface | 112 |
| Lower Surface | 113 |
| Groove | 114 |
| Projection | 115 |
| Narrowing | 116 |
| Rail | 117 |
| Pin Hole | 118 |
| Retention Pin | 120 |
| Rod Attachment Assembly | 130 |
| Slide Body | 140 |
| Recess | 141 |
| Rail Aperture | 142 |
| Retention Ring | 150 |
| Saddle Body | 160 |
| Axial Channel | 161 |
| Locking Threads | 162 |
| Stabilizing Rod Slot | 163 |
| Shoulder | 164 |
| Recess | 165 |
| Wave Spring | 170 |
| Pressure Cap | 180 |
| Pressure Cap Surface | 181 |
| Flange | 182 |
| Upper Flange Surface | 183 |
| Groove | 184 |

DETAILED DESCRIPTION

The present disclosure relates, in some embodiments, to an implantable orthopedic assembly generally comprising an occipital plate and one or more repositionable clamping assemblies for securing a stabilizing rod at a nonzero distance from a plate surface. One or more rails may extend laterally from a plate to support a clamping assembly.

Embodiments of a clamping assembly may comprise a base component (e.g., a slide body), a body component (e.g., a saddle body), and a locking component (e.g., a pressure cap). When unlocked, a clamping assembly may be laterally repositioned along a supporting rail and may also be rotationally repositioned. Locking occurs when a stabilizing rod is secured in a clamping assembly. The rod exerts a force upon the locking component, causing the locking component to exert a force upon the supporting rail. This force pulls a surface of a base component into a surface of a rail, effectively locking the base component at a fixed position. A clamping assembly may further comprise a loading component (e.g., a spring) to exert a stabilizing force on the locking component, keeping the clamping assembly positionally stable while adjustments are made prior to locking.

Figure 1B:
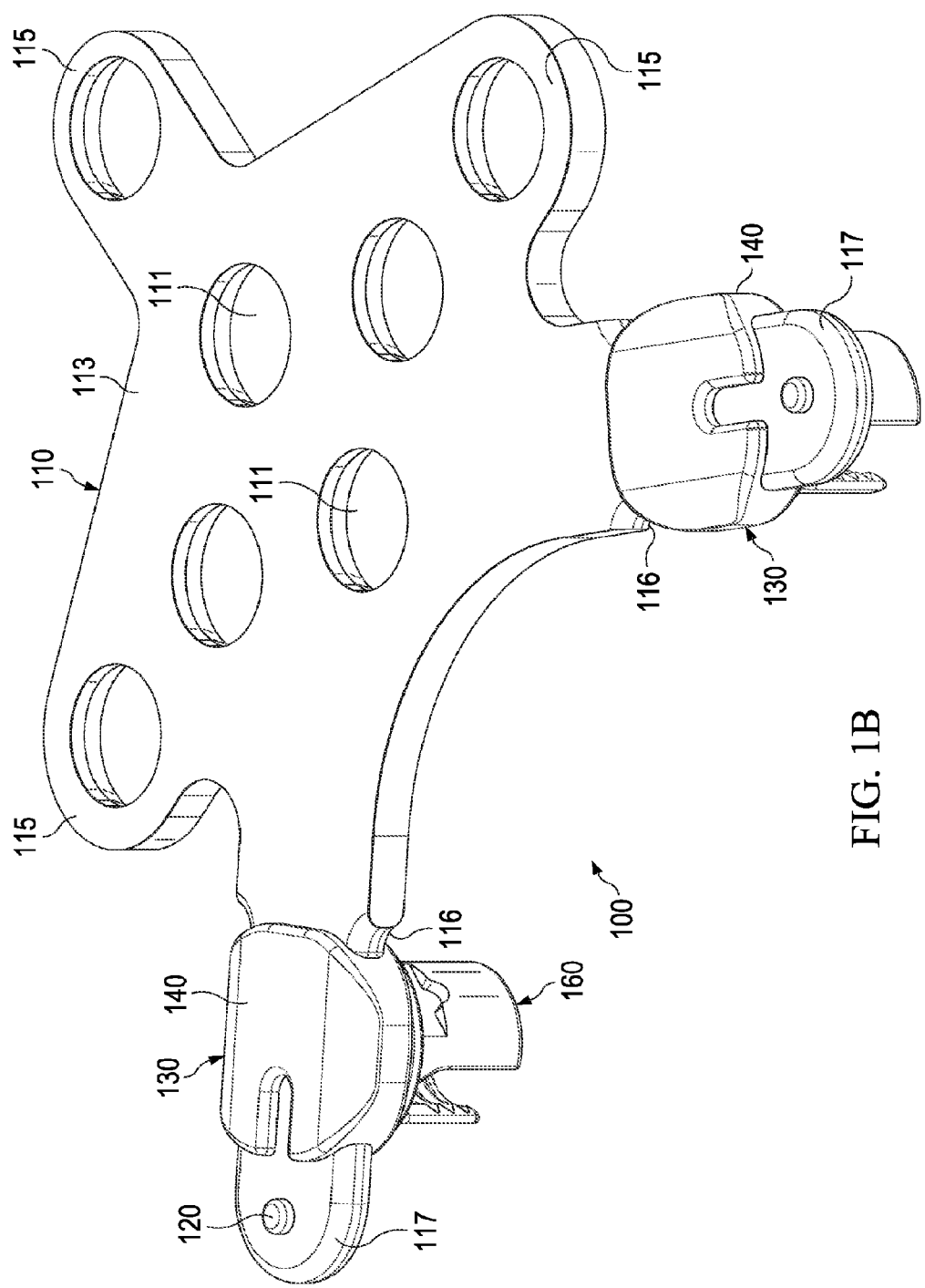
FIG. 1B illustrates a perspective view of an occipital-cervical fixation assembly according to a specific example embodiment of the disclosure.
Figure 1D:
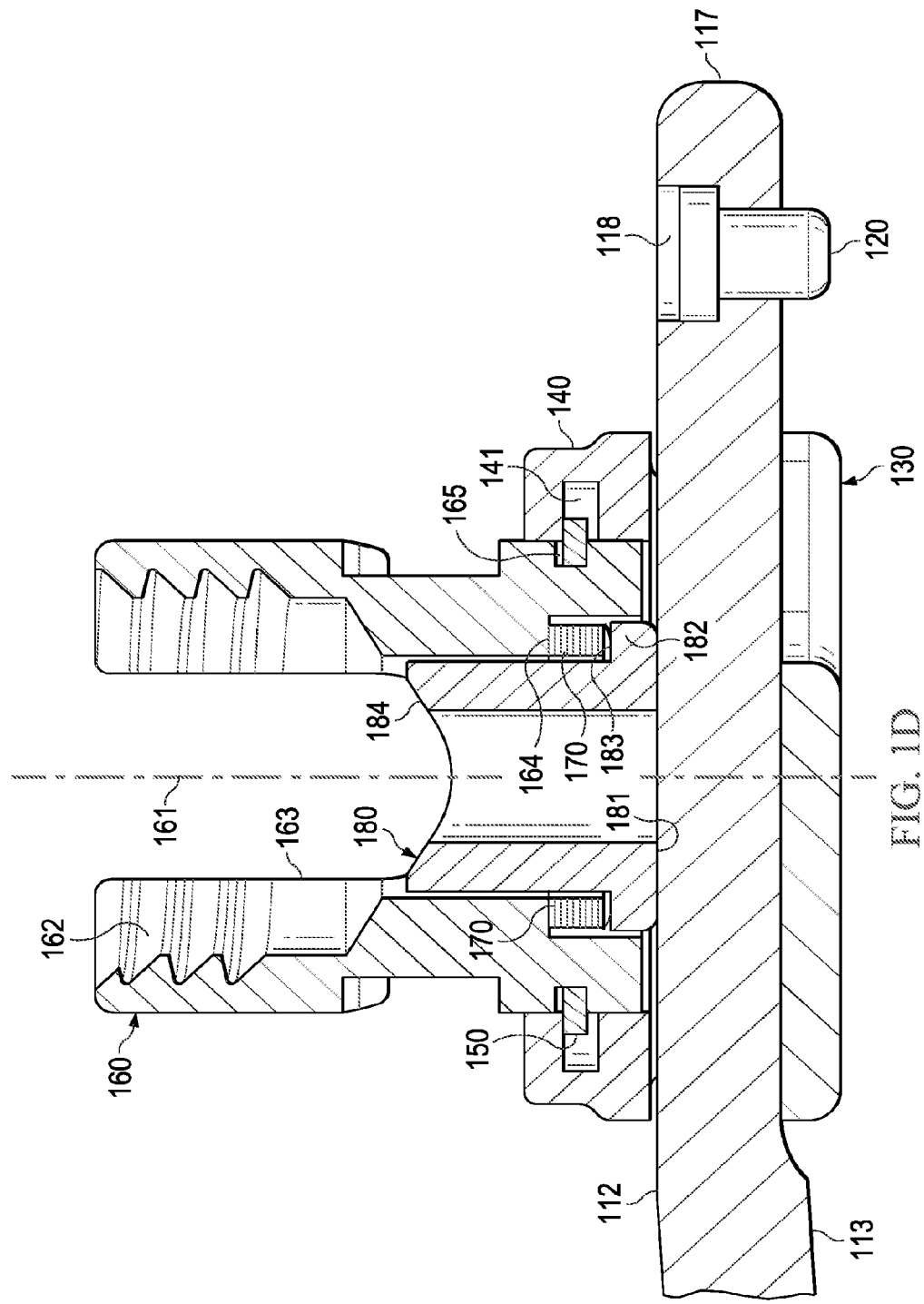
FIG. 1D illustrates a section view of an occipital-cervical fixation assembly according to a specific example embodiment of the disclosure.

Some embodiments of the disclosure are illustrated in FIG. 1A (upper perspective view), FIG. 1B (lower perspective view), FIG. 1C (section view), FIG. 1D (section view), FIG. 1E (exploded view), FIG. 1F (upper perspective view), FIG. 1G (section view).

Occipital Plate

In some embodiments, an occipital plate may be of any size and shape appropriate for being secured to an occiput. For example, an occipital plate may be configured to provide a rod spacing of about 20 mm to about 30 mm, about 30 mm to about 40 mm, or about 40 mm to about 50 mm. For example, when rod attachment assemblies are spaced at their outer most location, the rods are approximately 50 mm apart and when they are at their closest spacing the rods are approximately 40 mm apart for a 40-50 mm plate assembly. An occipital plate may be generally planar with an upper and lower surface, in some embodiments. An occipital plate may be made, according to some embodiments, from any material suitable for implantation into the body, including, for example, stainless steel, titanium, ceramic, PEEK, a composite material, and/or combinations thereof.

According to some embodiments, a disclosed assembly may be connected to one or more rods that are also connected to one or more cervical vertebrae. These rods may be connected to the cervical vertebra through the use of pedicle screws, such as the screws described in U.S. Pat. No. 6,540,748 and U.S. Published Patent Application No. 2010/0256681, both of which are owned by Blackstone Medical, Inc. and which are incorporated herein by reference.

An embodiment of occipital plate 110 is illustrated in FIG. 1A. As shown, occipital plate 110 is generally planar with an upper surface 112 and a lower surface 113. An occipital plate may support one or more rod attachment assemblies 130. An occipital plate may be secured to an occiput, and a stabilizing rod (not shown) may be secured in one or more rod attachment assemblies 130 to provide stabilization and/or promote fusion of the occipitocervical junction according to some embodiments.

Rails

An occipital plate may include, in some embodiments, one or more rails to bear one or more rod attachment assemblies. The shape and/or number of rails may be arranged around a point or axis (e.g., a central point or central axis). Each rail may run radially, laterally, longitudinally, and/or in any other direction. Each rail independently may be of the same and/or different length and/or with compared to other rails, in some embodiments. For example, two rails in symmetrical positions on a plate may have the same length and width. A rail may have a proximal end defined by a narrowing in plate body width and/or thickness, relative to the adjacent portion of the plate. A narrowing may be configured to restrict movement of a rod attachment assembly along a rail, for example, movement toward a central plate axis. A rail may include, at or adjacent to its distal end, a retention structure configured to limit movement of a rod attachment assembly along a rail, for example, movement away from a central plate axis. A retention structure may comprise a thickening in a rail in some embodiments. A retention structure may comprise, according to some embodiments, a retention pin, for example, installed in a pin hole and protruding from a rail.

Rails may be located on a proximal portion of occipital plate 110. For example, as shown in FIGS. 1A and 1B, occipital plate 110 may include two opposed rails 117. Each rail 117 has a narrowing 116 at its proximal end and a pin hole 118 at its distal end configured to accommodate retention pin 120. Narrowing 116 is depicted here as a narrowing in thickness, but rail 117 may be narrowed in thickness and/or width compared to the adjacent portion of plate 110. Although two rails are illustrated, embodiments are contemplated in which a plate comprises one rail, three rails or more than three rails.

Projections

An occipital plate may include one or more projections in some embodiments. The shape and/or number of projections may be arranged around a point or axis (e.g., a central point or central axis). Projections, according to some embodiments, may extend radially, laterally, longitudinally, and/or in any other direction. Each projection independently may be of the same and/or different length and/or with compared to other projections, in some embodiments.

Projections may be located on a distal portion of an occipital plate. For example, as shown in FIGS. 1A and 1B, occipital plate 110 may include one central projection 115 at its proximal apex and two opposed lateral projections 115. Although three projections are illustrated, embodiments are contemplated in which a plate comprises one projection, two projections, four projections or more than four projections.

Apertures

A plate may also comprise one or more apertures for receiving bone fasteners that may secure the plate to the occiput. Apertures may be circular or non-circular, may be countersunk, and may be orthogonal or non-orthogonal to the plate.

As shown in FIGS. 1A and 1B, multiple apertures 111 may be located on occipital plate 110. One or more such apertures may be arranged in any configuration across occipital plate 110. Such apertures may penetrate both upper surface 112 and lower surface 113, and may provide for attachment of occipital plate 110 to the occiput with bone fasteners (not shown) such as bone screws, pins, staples, or any other appropriate fasteners. An aperture 111 may be circular, oval, polygonal, or any other shape about a center axis that is suitable to accommodate an appropriate fastener.

Furthermore, the center axis of an aperture 111 may be orthogonal to the surface of occipital plate 110, such that a bone faster seated within aperture 111 enters the occiput orthogonally, or the center axis of an aperture 111 may be non-orthogonal to the surface of occipital plate 110, such that a bone faster seated within aperture 111 enters the occiput at an acute angle, providing for more contact between bone and fastener. In addition, aperture 111 may be countersunk such that the head of a bone fastener seated within aperture 111 is flush with or recessed from the top surface of occipital plate 110. Aperture 111 may also be counter-bored or otherwise shaped to accommodate a variety of bone fasteners. Multiple apertures 111 distributed across occipital plate 110 may be of uniform size and shape or may be of variable (e.g., independently variable) size and shape.

It is contemplated that occipital plate 110 may not utilize any apertures 111. In such embodiments, other methods of securing the occipital plate to the occiput are employed. For example, the occipital plate may be secured to the occiput with an adhesive, or fixation elements that penetrate the occiput may be integrated with the occipital plate, thereby eliminating the need for separate bone fasteners. Furthermore, notches or other guide features for interfacing with instruments external to occipital plate 110 may be located on occipital plate 110. Such instrument interfaces may allow a tool to be attached to facilitate placement, adjustment, and other manipulation of occipital plate 110.

Grooves

Embodiments of an occipital plate may comprise grooves for facilitating contouring of the plate. A plate may also comprise notches or other instrument interfaces for facilitating manipulation of the plate prior to and/or during placement.

Grooves 114 may be scored into upper surface 112 and/or lower surface 113 of occipital plate 110, for example, to provide for easier and more precise contouring and reshaping of occipital plate 110. Such grooves 114 may allow better correlation with the surface of the occiput. Grooves 114 may be of varying length, width, and depth, and may extend radially, laterally, longitudinally, or in any other direction. Although FIGS. 1A, 1B, and 1C illustrate occipital plate 110 with multiple grooves 114, an occipital plate 110 with a single groove 114 or no grooves 114 is contemplated.

Each rail 117 comprises a pin hole configured to fixedly or movably house corresponding retention pin 120. For example, retention pin 120 may be mounted in a position (e.g., a fixed position) protruding from surface 112 and/or 113. Retention pin 120 may alternatively be retractable within pin hole 118 and configured to have a deployed position in which it protrudes from surface 112 or 113 and an undeployed position in which it protrudes from neither surface 112 or 113. Rings, springs, detents, or other suitable means may be used to hold pin 120 in its deployed position and/or undeployed position.

Clamping Assembly

Rod attachment assembly 130 may be of any size and shape appropriate for securing a stabilizing rod to an occipital plate, and may be made from any material suitable for implantation into the body, such as stainless steel, titanium, ceramic, PEEK, or a composite material. Rod attachment assembly 130 comprises slide body 140, retention ring 150, saddle body 160, wave spring 170, and pressure cap 180. Slide body 140 defines aperture 142 sized to accommodate (e.g., slidably accommodate) rail 117. Slide 140 incorporates a clearance fit with a rail such that rod assembly 130 can move within a confined space between an undercut portion of a plate and a retention pin. Wave spring 170 is sandwiched between pressure cap 180 and a bore in saddle body 160 such that the spring applies force to pressure cap 180 causing a friction fit between the plate, slide, and pressure cap so force (e.g., light force) needs to be applied to slide rod attachment assembly 130 along a plate.

Slide Body

In some embodiments, a rod attachment assembly may include a slide body having a central rail aperture sized and shaped to receive a plate rail. A central aperture may surround, according to some embodiments, an engaged plate rail. A rail aperture may define a lateral axis of a slide body. A lateral axis may be parallel to a lateral (or radial) axis of a rail with which it is engaged. A slide body may have an aperture perpendicular to a rail aperture configured to receive, for example, a saddle body. A slide body aperture may include a recess, for example, around the circumference of the aperture. A slide body aperture recess may be configured to receive at least a portion of a retention ring. A slide body aperture recess may be positioned within the aperture such that it aligns with a corresponding recess in an engaged saddle body. A slide body aperture recess and a corresponding saddle body recess, together with an engaged retention ring may configured to position and/or hold a saddle body within a desired distance (e.g., a fixed distance, a pre-selected distance, a variable distance within a defined range) of an engaged rail, in some embodiments. As shown in FIG. 1C, for example, slide body aperture recess 141, retention ring 150, and saddle body recess 165 together may position and hold slide body 140 and saddle body 160 together and hold saddle body at a distance from rail 117.

Saddle Body

Saddle body 160 incorporates slot 163 (e.g., to receive a rod) and locking thread 162 (e.g., to receive a set screw to clamp the rod to saddle body 160 and/or rod attachment assembly 130). As a set screw is tightened to secure a rod, pressure cap 180 forces an associated occipital plate rail 117 against slide 140's plate interface bottom surface, locking the position of rod attachment assembly 130 along the occipital plate rail 117. Saddle body 160's orientation is simultaneously locked such that rotation of saddle body 160 about its axis is locked. This is the result of saddle body 160 being pulled upward forcing retention ring 150 against the upper surface of recess 141 in slide 140 in which the retention ring 150 is housed.

Pressure Cap

According to some embodiments, a rod attachment assembly may include a pressure cap. For example, saddle body 160, in some embodiments, may comprise axial channel 161 configured to receive wave spring 170 and/or pressure cap 180. According to some embodiments, a pressure cap may slide within an axial channel of a saddle body (e.g., up and down with respect to the plane of an associated plate).

In some embodiments, a pressure cap may have any shape including, for example, a generally cylindrical shape. Its center or core may be solid or hollow, as desired. It's lower end may be configured to contact a plate rail (e.g., on a lower surface). For example, the lower (outer) circumference may include a flange configured to increase the contact surface area. A flange may include an upper surface configured to contact a spring (e.g., a wave spring). An upper end of a pressure cap may include a groove or detent configured to engage a set screw and/or a rod. For example, as shown in FIG. 1C, pressure cap 180 has hollow core and includes lower surface 181, flange 182, wave spring surface 183, and groove 184. If rod engagement cut out geometry 184 is incorporated on pressure cap 180, some orientation control of that geometry relative to slot 163 may be beneficial. Pressure cap 180 may only contact saddle body 160 in regard to orientation (rotation control). A pressure cap may be cylindrical with two milled flats that are perpendicular to the cut out that accepts the rod in some embodiments. Any desirable means for ensuring a pressure cap cut out is aligned with the slot in the saddle body to enable proper rod engagement may be used, according to some embodiments.

Retention Ring

According to some embodiments, a rod attachment assembly may include a retention ring configured, for example, to engage a slide body and/or saddle body. A retention ring may be configured to have a desired or required rigidity against forces perpendicular to the plane of the ring. In some embodiments, a retention ring may be configured to deform to permit insertion and/or engagement of a saddle body. For example, a retention ring may have radial elasticity and/or resilience.

Loading Component

A rod attachment assembly, in some embodiments, may include a loading component configured, for example, to resist axial forces and/or axial movement of a pressure cap (e.g., resist longitudinal forces and/or movement that would otherwise tend to bring pressure cap into closer proximity to a saddle body). For example, a loading component may comprise spring 170 positioned between pressure cap 180 and saddle body 160 and configured to resist movement and/or forces that would otherwise bring pressure cap flange surface 182 into closer proximity to saddle body shoulder 164.

In some embodiments, a loading component may exert a stabilizing force on a locking component to keep a rod attachment assembly positionally stable prior to locking. Such a loading component allows for more precise lateral and rotational positioning of rod attachment assembly 130. In the embodiment illustrated in FIG. 1C, the loading component 170 is represented by a wave spring located between saddle body component 160 and pressure cap 180. Wave spring 170 exerts a light pressure on pressure cap 180 to act as a load to the system. This load imparts a friction to the system, keeping rod attachment assembly 130 positionally stable. Although a wave spring is depicted in FIG. 1C, other suitable methods of loading the system are contemplated.

Wave spring 170 may also apply force to saddle body 160 which results in a friction fit between saddle body 160, retention ring 150, and slide 140. This necessitates light force being applied to enable rotation of saddle body 160 about slide 140. The friction fit enables adjustments to be made while eliminating fiddle factor of components inadvertently moving.

Operation

Occipital plate 110 supports one or more rod attachment assemblies 130. Although FIGS. 1A, 1B, and 1C illustrate embodiments with two clamping assemblies, embodiments with a single clamping assembly and embodiments with three or more clamping assemblies are contemplated. Occipital plate 110 may be secured to an occiput, and a stabilizing rod (not shown) may be secured in one or more rod attachment assemblies 130 to provide stabilization and/or promote fusion of the occipitocervical junction.

Each rod attachment assembly 130 has at least two states: locked and unlocked. In its unlocked state, each rod attachment assembly 130 is movably attached to a portion of occipital plate 110 (e.g., rail 117) and may be adjusted positionally prior to locking. For example, rod attachment assembly 130 may be repositioned laterally by sliding rod attachment assembly 130 along a portion of occipital plate 110. Rod attachment assembly 130 may be repositioned rotationally, for example, by turning rod attachment assembly 130 about an axis substantially orthogonal to occipital plate 110. In its unlocked state, a rod attachment assembly may be prevented from disconnecting completely from an occipital plate, for example by a retaining element located on the occipital plate or on the rod attachment assembly. For example, rod attachment assembly 130 may be prevented from disconnecting completely from rail 117 of occipital plate 110 by retaining pin 120 located at the distal end of rail 117.

In some embodiments, an unlocked rod attachment assembly 130 may be fully disconnected from an occipital plate. According to some embodiments, rod attachment assembly 130 may be configured with a loading component to positionally stabilize unlocked rod attachment assembly 130, allowing for positioning (e.g., more precise positioning) prior to locking.

Once rod attachment assembly 130 is properly positioned, rod attachment assembly 130 may be locked in place. Once locked, rod attachment assembly 130 is rigidly fixed to occipital plate 110, and further lateral and rotational movement of rod attachment assembly 130 relative to occipital plate 110 is precluded. Locking occurs when a stabilizing rod (not shown) is inserted into rod attachment assembly 130. The adjustability of rod attachment assembly 130 relative to occipital plate 110 prior to locking, along with the simplicity of the locking procedure, allows the installation of occipitocervical fixation assembly 100 to be quickly and easily customized to accommodate variations in patient anatomy as well as variations in desired therapeutic benefits.

Clamp assembly variants may incorporate ball bearings to secure a saddle body to a slide body or may have a band welded to a portion of a saddle body. According to some embodiments, a retention ring (e.g., ring 150) may replace such balls, for example, to reduce or eliminate localized loading, reduce the height (h) of rod attachment assembly, and/or to improve engagement between a saddle body and a slide 140 since the recess to house a retention ring is smaller than the cavity needed to accommodate balls.

As shown in FIGS. 2-4, the fixation apparatus may impact the height (h) that a clamp assembly rises above an upper surface of an associated plate. Rod attachment assembly 200, which includes a retention ring, has the smallest height (h). Clamp assembly 300 with ball bearings, has an intermediate height (h). Clamp assembly 400 with ball bearings, is the tallest. As shown, rod attachment assemblies 200, 300, and 400 accommodate plates having the same thickness. The overall height of assembly 200 was reduced with a design that increases the strength of the assembly while incorporating a stiffer plate.

To construct an embodiment of rod attachment assembly 130, wave spring 170 and pressure cap 180 may be positioned within axial channel 161 of saddle body 160. Retention ring 150 may be inserted in slide body recess 141. Saddle body 160 may be inserted into slide body 140 and retention ring 150 until saddle body recess 165 is engaged. Rod attachment assembly 130 may be mounted on plate body 110 by sliding it onto rail 117. Retention pin 120, if present, should be in an undeployed position while rod attachment assembly 130 is mounted and subsequently installed and/or moved to a deployed position.

As constructed, rod attachment assembly 130 in its unlocked state loosely encloses a portion of rail 117 and may be repositioned by sliding rod attachment assembly 130 along a portion of rail 117. In some embodiments, rod attachment assembly 130 may be repositioned at discrete points along rail 117; in other embodiments, rod attachment assembly 130 may be infinitely repositionable along rail 117. In some embodiments, rod attachment assembly 130 may be slid off the end of rail 117 and thus fully disconnected from rail. Rod attachment assembly 130 may be slid between two locations along rail 117 but a retaining element (e.g., retention pin 120) may prevent rod attachment assembly 130 from sliding off the end of rail 117. In its unlocked state, rod attachment assembly 130 may also be repositioned rotationally. Such rotational repositioning allows for varying the angle at which a stabilizing rod inserted in slot 163 is positioned relative to rail 117.

According to some embodiments, a saddle body may be rotationally repositioned at discrete points throughout 360° of potential rotational freedom. In some embodiments, a saddle body may be infinitely repositionable throughout 360° of potential rotational freedom. In some embodiments, rod attachment assembly 130 may be rotationally repositioned in a finite number of positions; in other embodiments, rod attachment assembly 130 may be infinitely rotationally repositioned.

Both the lateral and rotational position of rod attachment assembly 130 may be locked by introducing a stabilizing rod (not shown) into slot 163. Locking threads 162 prevent the stabilizing rod from exiting slot 163, and in some embodiments a locking nut, locking cap, or other component (not shown) may be employed to secure the stabilizing rod in slot 163. In some embodiments, rod attachment assembly 130 is still fully or partially adjustable after the insertion of the stabilizing rod, but not after the stabilizing rod is fully secured. Exemplary apparatus that may be utilized to lock the rod within slot 163 are described in U.S. Pat. Nos. 6,540,748 and 8,062,339 and U.S. Published Patent Application No.

2010/0256681, each of which is owned by Blackstone Medical, Inc. and are hereby incorporated by reference.

A secured stabilizing rod in slot 163 contacts and exerts a force upon pressure cap 180, causing pressure cap 180 to exert a force upon the top surface of rail 117, pulling slide body 140 into contact with rail 117. This immobilizing force locks the position of rod attachment assembly 130 both laterally and rotationally, effectively locking the position of the stabilizing rod relative to the occipital plate with no direct contact between the stabilizing rod and slide body 140. In the embodiment of FIG. 1C, pressure cap 180 is a rod-to-plate locking pin located between saddle body 160 and rail 117.

Although the present invention has been described in detail, it should be understood that various changes, substitutions, and alterations can be made without departing from the spirit and scope of the invention as defined by the appended claims. Various terms used herein have special meanings within the present technical field. Whether a particular term should be construed as such a "term of art" depends on the context in which that term is used. "Connected to," "coupled to," "secured to," "in contact with," or other similar terms should generally be construed broadly. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.P.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

As will be understood by those skilled in the art who have the benefit of the instant disclosure, other equivalent or alternative compositions, devices, methods, and systems for stabilizing the occipitocervical junction and the cervical spine can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of rod attachment assemblies may be varied. In some embodiments, plates, retention pins, rod attachment assemblies, slide bodies, retention rings, saddle bodies, loading components, and/or pressure caps may be interchangeable. Interchangeability may allow fit to a subject to be custom adjusted. In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for stabilizing the occipitocervical junction and the cervical spine may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

What is claimed is:

1. A method of constructing an implantable orthopedic assembly comprising an occipital plate, at least one rail rigidly coupled to and extending laterally from the occipital plate, and at least one repositionable rod attachment assembly enclosing a portion of the at least one rail, the at least one repositionable rod attachment assembly adapted for securing a received portion of a stabilizing rod, the method comprising:

positioning a pressure cap of the repositionable rod attachment assembly within a receptacle of a saddle body of the at least one repositionable rod attachment assembly, the pressure cap having a rod contacting surface at a first side and an outwardly extending flange at a second side distal to the first side;

positioning a surface of the at least one rail against a surface of a slide body of the at least one repositionable rod attachment assembly;

installing a retention ring in inside the slide body;

positioning a loading component between the pressure cap and the saddle body of the at least one repositionable rod attachment assembly such that the loading component is in contact with the outwardly extending flange of the pressure cap, the loading component being adapted to exert a bias on the pressure cap against the at least one rail to stabilize the at least one repositionable rod attachment assembly at an adjustable rail position and in an adjustable body position;

uniting the saddle body with the slide body, wherein the at least one rail contacts the pressure cap; and securing the slide body to the saddle body with the retention ring disposed in an outer circumferential recess of the saddle body.

2. The method of claim 1, further comprising facilitating manipulation of at least one instrument interface of the occipital plate.

3. The method of claim 1, further comprising laterally repositioning the slide body of the at least one repositionable rod attachment assembly between a first rail position and a second rail position.

4. The method of claim 1, further comprising rotationally repositioning the saddle body of the at least one repositionable rod attachment assembly between a first body position and a second body position.

5. The method of claim 1, further comprising exerting a stabilizing force on the pressure cap with the loading component.

6. The method of claim 5, further comprising stabilizing the at least one repositionable rod attachment assembly at an adjustable rail position and in an adjustable body position with the stabilizing force.

7. The method of claim 1, further comprising at least partially enclosing a portion of the at least one rail with a slot in the slide body.

8. The method of claim 1, wherein the rod contacting surface comprises a groove at one end of the pressure cap.

9. The method of claim 1, further comprising attaching a retaining element to the at least one rail.

10. The method of claim 9, further comprising preventing the slide body from sliding off an end of the at least one rail with the retaining element.

11. The method of claim 1, further comprising locking the at least one repositionable rod attachment assembly along the at least one rail in a locked state.

12. The method of claim 1, further comprising positionally adjusting the at least one repositionable rod attachment assembly along the at lease one rail in an unlocked state.

13. The method of claim 1, wherein a plurality of apertures is variably distributed across the occipital plate, wherein the plurality of apertures penetrates both a top surface of the occipital plate and a bottom surface of the occipital plate, and wherein at least one of the plurality of apertures is adapted to receive at least one bone fastener.

14. The method of claim 13, further comprising securing the bottom surface of the occipital plate to an occiput with the at least one bone fastener.

15. The method of claim 1, wherein the retention ring includes a split ring.

16. The method of claim 1, wherein the step of uniting occurs after the step of installing.

17. The method of claim 1, wherein the loading component includes a spring.

18. The method of claim 17, wherein the spring includes a wave spring.

* * * * *